United States Patent [19]

McGibbon

[11] Patent Number: 5,260,466
[45] Date of Patent: Nov. 9, 1993

[54] PREPARATION OF TITANIUM DERIVATIVES

[75] Inventor: Graeme McGibbon, Whitley Bay, England

[73] Assignee: Tioxide Specialties Limited, London, England

[21] Appl. No.: 926,292

[22] Filed: Aug. 10, 1992

[30] Foreign Application Priority Data

Aug. 8, 1991 [GB] United Kingdom ........... 9117191

[51] Int. Cl.$^5$ .............................. C07F 7/28
[52] U.S. Cl. ................................. 556/55
[58] Field of Search ........................ 556/55

[56] References Cited

U.S. PATENT DOCUMENTS

| | | | |
|---|---|---|---|
| 2,621,193 | 12/1952 | Langkammerer | 260/414 |
| 2,621,195 | 12/1952 | Haslam | 260/414 |
| 2,870,181 | 1/1959 | Shacklett | 260/429.5 |
| 2,898,356 | 8/1959 | Russell | 260/429.5 |

FOREIGN PATENT DOCUMENTS

| | | |
|---|---|---|
| 1539228 | 9/1968 | France . |
| 50-107031 | 8/1975 | Japan . |
| 2089690 | 4/1987 | Japan . |
| 757190 | 11/1954 | United Kingdom . |
| 1091525 | 11/1967 | United Kingdom . |

*Primary Examiner*—José G. Dees
*Assistant Examiner*—Porfikio Nazario
*Attorney, Agent, or Firm*—Baker & Botts

[57] ABSTRACT

A new method for the production of titanium derivatives of carboxylic acids is provided. A liquid or solid carboxylic acid is suspended in an inert liquid diluent in which it is substantially insoluble and reacted with a titanium alkoxide to form a titanium derivative which is also substantially insoluble in the inert diluent.

The invention provides a simple method for the production of titanium compounds which are easily transported and can readily be dissolved in water for use, for example, as catalysts and cross-linking agents.

17 Claims, No Drawings

PREPARATION OF TITANIUM DERIVATIVES

This invention relates to the preparation of titanium compounds and in particular to the preparation of titanium derivatives of carboxylic acids.

Organic titanium compounds have been widely used in numerous applications including, for example, as esterification or polymerisation catalysts, as cross-linking agents and as intermediates for producing titanium oxide films or titanium oxide catalysts.

In using organic titanium compounds for certain applications it is advantageous to employ a titanium compound which can be dissolved in water since this can avoid handling problems, particularly those associated with the handling of flammable liquids.

It is an object of this invention to provide a simple method for the preparation of organic titanium compounds which are readily soluble in water and which are produced in a stable form in which they are easily stored and transported.

According to the invention a method for the preparation of a titanium derivative of a carboxylic acid comprises forming a mixture of a solid or liquid carboxylic acid with an inert liquid diluent and reacting the carboxylic acid in the mixture with a titanium alkoxide so as to precipitate said titanium derivative said carboxylic acid and said titanium derivative being substantially insoluble in said inert liquid diluent.

The method can be used with any carboxylic acid which is a solid or a liquid at the temperature of the reaction. It is particularly suitable for use with solid acids such as oxalic acid or citric acid either in their anhydrous forms or as hydrates and when used with solid acids a suspension of the acid in the diluent is formed. An example of a liquid acid is lactic acid (88%) and when used the mixture has the form of dispersed droplets of acid in the diluent.

The carboxylic acid is mixed with an inert liquid diluent. This diluent can be any liquid in which the acid and the titanium derivative which is the product of the preparation are substantially insoluble. Preferred diluents are chlorinated hydrocarbons such as chloroform and carbon tetrachloride or hydrocarbons such as toluene, benzene, cyclohexane, hexane, heptane and petroleum fractions such as petroleum ether.

The mixture is most conveniently formed by stirring the mixture of diluent and carboxylic acid but any other suitable means of formation such as ultrasonic agitation may be employed.

The concentration of the carboxylic acid in the mixture is conveniently from 50 to 3000 g/liter and preferably 400 to 600 g/liter.

In the preparation of some titanium derivatives by the method of this invention it is convenient to avoid the presence of water since this may cause premature hydrolysis during storage. The anhydrous form of the carboxylic acid can therefore be employed but, alternatively, when a hydrated form is used then the hydrated carboxylic acid is suspended in the inert diluent and the carboxylic acid is dehydrated by removing the water of crystallisation as a co-distillate with a proportion of the inert diluent before reaction of the acid with a titanium alkoxide.

Any titanium alkoxide which will react with the carboxylic acid can be used in the process of this invention but usually, for economy and convenience, a titanium alkoxide derived from an alcohol containing up to eight carbon atoms will be employed. Particularly useful titanium alkoxides are titanium tetraethoxide, titanium tetrabutoxide, titanium tetraisopropoxide and titanium tetrakis(2-ethylhexoxide).

These titanium alkoxides can be dissolved in the inert diluent and the carboxylic acid can be suspended in the solution so formed but it is generally more convenient to suspend the acid in the inert diluent and add the titanium alkoxide which is usually a liquid.

The reaction between the acid and the titanium alkoxide can be carried out at any temperature up to the boiling point of the inert diluent. However, reaction can usually be accomplished in a relatively short time at room temperature and reaction at room temperature is therefore preferred.

The reaction mixture of suspension and titanium alkoxide is agitated for sufficient time to allow complete reaction of the carboxylic acid with the titanium alkoxide and the product is then generally separated from the inert diluent and by-products. Typically, the solid product is separated by filtration, washed with a portion of the inert diluent and allowed to dry at room temperature or in an oven at elevated temperature.

A number of different products can be formed by varying the molar ratio of titanium alkoxide to carboxylic acid thereby forming products containing different proportions of residual alkoxide groups.

The method is most usefully employed to produce a titanium derivative which forms a stable aqueous solution and such products generally contain a relatively low proportion of residual alkoxide groups. Preferably, the molar ratio of titanium alkoxide to carboxylic acid employed is sufficient to ensure that substantially all the alkoxide groups are replaced by carboxylic acid groups. For example, when the carboxylic acid used is oxalic acid the molar ratio titanium alkoxide to oxalic acid is preferably from 1:0.5 to 1:4 and most preferably about 1:2. When citric acid is used the ratio is preferably from 1:05 to 1:4 and most preferably 1:1 to 1:1.33.

The products of the method of this invention are stable solids which are easy to transport and are readily soluble in water. The aqueous solutions obtainable from these products can contain relatively high concentrations of titanium by comparison with similar products made by known processes. For example, solutions of titanium oxalate containing over 9% by weight titanium calculated as Ti can be prepared.

The products of the method of the invention find use as catalysts and cross-linking agents and can be employed in aqueous solution to coat a variety of substrates. When coated on substrates they can generally be decomposed readily on heating to form a coating of titanium oxide which may be employed as a protective film or as a catalyst.

The invention is illustrated by the following Examples.

EXAMPLE 1

Tetraisopropyl titanate (142 g, 0.5 mole) was added dropwise to a vigorously agitated mixture of anhydrous oxalic acid (90 g, 1 mole) in petroleum ether (Exxsol Heptane) (340 g) over a period of twenty minutes.

The resulting white precipitate was separated by filtration and the resulting filter cake washed with fresh petroleum ether (3×150 ml). The filter cake was sucked dry on the filter.

The resulting powder had a titanium content of 13.24% (as Ti), and a total isopropanol content of

EXAMPLE 2

Tetraisopropyl titanate (142 g, 0.5 mole) was added dropwise to a vigorously agitated mixture of oxalic acid dihydrate (126 g, 1 mole) in petroleum ether (Exxsol Heptane) (340 g) over a period of twenty minutes.

The resulting white precipitate was separated by filtration and the resulting filter cake washed with fresh petroleum ether (3×150 ml). The filter case was sucked dry on the filter.

The resulting powder had a titanium content of 13.46% (as Ti), and a total isopropanol content of 9.4%. This solid was readily soluble in demineralised water at 25° C. to give a solution containing 9.76% Ti by weight.

EXAMPLE 3

Tetraisopropyl titanate (142 g, 0.5 mole) was added dropwise to a vigorously agitated mixture of oxalic acid dihydrate (94.5 g, 0.75 mole) in petroleum ether (Exxsol Heptane) (340 g) over a period of twenty minutes. The resulting mixture was then left to stir for a further forty five minutes. The resulting white precipitate was separated by filtration and the resulting filter cake washed with fresh petroleum ether (3×150 ml). The filter cake was sucked dry on the filter.

The resulting powder had a titanium content of 19.31% (as Ti), and a total isopropanol content of 2.5%. This solid was readily soluble in demineralised water at 25° C. to give a solution containing 9.45% titanium by weight.

EXAMPLE 4

Oxalic acid dihydrate (756 g, 6 mole) was added to petroleum ether (Exxsol Heptane) (1000 g) and agitated vigorously. Petroleum ether was heated to reflux and water removed by use of Dean and Stark apparatus. After the theoretical amount of water had been removed tetraisopropyl titanate (852 g, 3 moles) was added over a period of 45 minutes. After the addition of the tetraisopropyl titanate the resulting mixture was stirred for a further 60 minutes.

The resulting white precipitate was separated by filtration and the resulting filter cake washed with fresh petroleum ether (2×400 ml). The filter cake was sucked dry on the filter.

The resulting white powder had a titanium content of 23.75% (as Ti), and a total isopropanol content of 10.5%. This solid was readily soluble in demineralised water at 25° C. to give a solution containing 11.25% Ti by weight.

EXAMPLE 5

Tetraisopropyl titanate (142 g, 0.5 mole) was added dropwise to a vigorously agitated mixture of citric acid monohydrate (69.72 g, 0.332 moles) and anhydrous citric acid (63.74 g, 0.332 moles) in petroleum ether (Exxsol Heptane) (360 g) over a period of twenty minutes.

The resulting slurry was then refluxed for 90 minutes and the resulting white precipitate was separated by filtration. The resulting cake was sucked dried for 2 hours on the filter and then oven dried at 100° C. for 90 minutes, to give a solid with a titanium content of 14.46% (wt/wt).

This solid was readily soluble in demineralised water to give a solution containing 9% titanium by weight.

EXAMPLE 6

Tetraisopropyl titanate (142 g, 0.5 mole) was added dropwise to a vigorously agitated mixture of lactic acid (102.27 g of an 88% aqueous solution) in petroleum ether (Exxsol Heptane) (360 g).

The resulting slurry was stirred at room temperature for 90 minutes and the resulting white precipitate was separated by filtration. The resulting cake was sucked dried for 2 hours on the filter and then oven dried at 100° C. for 30 minutes to give a powder with a Ti content of 20.1% (wt/wt).

This solid was readily soluble in demineralised water to give a solution containing 9.23% titanium by weight.

EXAMPLE 7

Lactic acid (102.27 g of an 88% aqueous solution) was added to petroleum ether (Exxsol Heptane) (360 g) and agitated vigorously. The petroleum ether was heated to reflux and water was removed by the use of a Dean and Stark apparatus.

After the theoretical amount of water had been removed and the pot temperature had cooled down to room temperature, tetraisopropyl titanate (142 g, 0.5 mole) was added over a period of twenty minutes. After the addition of the tetraisopropyl titanate the resulting mixture was stirred for a further 90 minutes.

The resulting white precipitate was separated by filtration and the resulting filter cake sucked dry for 2 hours on the filter, and then oven dried at 120° C. for 30 minutes to give a solid with a titanium content of 19.00% (wt/wt). This solid was readily soluble in demineralised water to give a solution containing 9.02% titanium by weight.

EXAMPLE 8

Oxalic acid dihydrate (252 g, 1.17 moles) was added to petroleum ether (Exxsol Heptane) (700 g) and agitated vigorously. The petroleum ether was heated to reflux and water removed by use of a Dean and Stark apparatus. After the theoretical amount of water had been removed and the pot temperature had cooled down to room temperature, tetraisopropyl titanate (284 g, 1 mole) was added over a 20 minute period. After the addition of the tetraisopropyl titanate the resulting mixture was stirred for further 90 minutes.

The resulting white precipitate was separated by filtration and the resulting filter cake sucked dry for 2 hours on the filter, and then oven dried at 100° C. for 2 hours to give a solid with a titanium content of 23.86% by weight.

This solid was readily soluble in demineralised water to give a solution containing 9.32% titanium by weight.

I claim:

1. A method for the preparation of a titanium derivative of a carboxylic acid comprising forming a mixture of a solid or liquid carboxylic acid with an inert liquid diluent and reacting the carboxylic acid in the mixture with a titanium alkoxide so as to precipitate said titanium derivative, said carboxylic acid and said titanium derivative being substantially insoluble in said inert liquid diluent.

2. A method according to claim 1 in which the carboxylic acid is selected from the group consisting of oxalic acid, citric acid and lactic acid.

3. A method according to claim 1 in which the carboxylic acid is an anhydrous carboxylic acid.

4. A method according to claim 1 in which the carboxylic acid is a hydrated carboxylic acid, the mixture is heated to reflux and water is removed as a co-distillate with a portion of the inert diluent before the carboxylic acid is reacted with the titanium derivative.

5. A method according to claim 1 in which the inert liquid diluent is a hydrocarbon or a chlorinated hydrocarbon.

6. A method according to claim 5 in which the inert liquid diluent is selected from the group consisting of chloroform, carbon tetrachloride, toluene, benzene, cyclohexane, hexane, heptane and petroleum fractions.

7. A method according to claim 1 in which the titanium alkoxide is derived from an alcohol containing up to eight carbon atoms.

8. A method according to claim 7 in which the titanium alkoxide is selected from the group consisting of titanium tetraethoxide, titanium tetraisopropoxide, titanium tetrabutoxide and titanium tetrakis(2-ethylhexoxide).

9. A method according to claim 1 in which the concentration of the carboxylic acid in the mixture is from 50 to 3000 grams per liter.

10. A method according to claim 9 in which the concentration is from 400 to 600 grams per liter.

11. A method according to claim 1 in which the amount of carboxylic acid used is sufficient to ensure that substantially all the alkoxide groups of the titanium alkoxide are replaced by carboxylic acid groups.

12. A method according to claim 1 in which the carboxylic acid is oxalic acid and the molar ratio titanium alkoxide:oxalic acid is from 1:0.5 to 1:4.

13. A method according to claim 12 in which the molar ratio is about 1:2.

14. A method according to claim 1 in which the carboxylic acid is citric acid and the molar ratio titanium alkoxide:citric acid is from 1:0.5 to 1:4.

15. A method according to claim 14 in which the molar ratio is from 1:1 to 1:1.33.

16. A method according to claim 1 in which the titanium alkoxide is added to the mixture of carboxylic acid and inert liquid diluent.

17. A method according to claim 1 in which the mixture of carboxylic acid and inert liquid diluent is formed by use of ultrasonic agitation.

* * * * *